(12) United States Patent
Biedermann et al.

(10) Patent No.: US 9,339,304 B2
(45) Date of Patent: May 17, 2016

(54) HIGH ANGULATION POLYAXIAL BONE ANCHORING DEVICE

(71) Applicant: Biedermann Technologies GmbH & Co. KG, Donaueschingen (DE)

(72) Inventors: Markku Biedermann, Miami, FL (US); José Santiago, Miami, FL (US)

(73) Assignee: Biedermann Technologies GmbH & Co. KG, Donaueschingen (DE)

(*) Notice: Subject to any disclaimer, the term of this patent is extended or adjusted under 35 U.S.C. 154(b) by 205 days.

(21) Appl. No.: 13/663,201

(22) Filed: Oct. 29, 2012

(65) Prior Publication Data

US 2013/0110178 A1 May 2, 2013

Related U.S. Application Data

(60) Provisional application No. 61/552,019, filed on Oct. 27, 2011.

(51) Int. Cl.
*A61B 17/04* (2006.01)
*A61B 17/86* (2006.01)
*A61F 2/08* (2006.01)
*A61B 17/70* (2006.01)
*A61B 17/00* (2006.01)

(52) U.S. Cl.
CPC .......... *A61B 17/7038* (2013.01); *A61B 17/7037* (2013.01); *A61B 2017/00858* (2013.01); *Y10T 29/49826* (2015.01)

(58) Field of Classification Search
USPC .................................. 606/257–279, 300–321
See application file for complete search history.

(56) References Cited

U.S. PATENT DOCUMENTS

| 6,248,105 | B1 | 6/2001 | Schläpfer et al. |
| 6,736,820 | B2 | 5/2004 | Biedermann et al. |
| 7,678,137 | B2 | 3/2010 | Butler et al. |
| 8,021,397 | B2 | 9/2011 | Farris et al. |
| 8,092,494 | B2 | 1/2012 | Butler et al. |

(Continued)

FOREIGN PATENT DOCUMENTS

| JP | 2010-515552 A | 5/2010 |
| WO | WO 2005/018471 A1 | 3/2005 |
| WO | WO 2008-089096 A2 | 7/2008 |

OTHER PUBLICATIONS

Extended European Search Report for European Application No. 12154115.5, European Search Report dated May 2, 2012 and mailed May 10, 2012 (8 pgs.).

*Primary Examiner* — Sameh Boles
(74) *Attorney, Agent, or Firm* — Lewis Roca Rothgerber Christie LLP

(57) ABSTRACT

A polyaxial bone anchoring device includes a bone anchoring element having a shank and a head, a receiving part having a first end and a second end, a central axis, a first bore, a second bore, and a first support surface between the first bore and the second bore that is substantially perpendicular to the central axis, and an insert piece having a seat for pivotably holding the head, a bounding edge, and a second support surface configured to engage the first support surface to support the insert piece when mounted to the receiving part, the second support surface formed by a projection at an end of the insert piece opposite the bounding edge, wherein the insert piece projects out of the second bore and is rotatable, and is configured to permit the bone anchoring element to pivot at a larger angle at a first location of the bounding edge.

21 Claims, 9 Drawing Sheets

(56) References Cited

U.S. PATENT DOCUMENTS

| | | |
|---|---|---|
| 8,337,530 B2 | 12/2012 | Hestad et al. |
| 8,409,260 B2 | 4/2013 | Biedermann et al. |
| 8,419,778 B2 | 4/2013 | Barry |
| 2004/0153077 A1 | 8/2004 | Biedermann et al. |
| 2005/0038430 A1 | 2/2005 | McKinley |
| 2005/0080415 A1 | 4/2005 | Keyer et al. |
| 2005/0154391 A1* | 7/2005 | Doherty et al. ............ 606/61 |
| 2005/0159750 A1 | 7/2005 | Doherty |
| 2007/0093819 A1* | 4/2007 | Albert ........................ 606/61 |
| 2007/0118123 A1 | 5/2007 | Strausbaugh et al. |
| 2007/0270842 A1 | 11/2007 | Bankoski et al. |
| 2008/0021473 A1 | 1/2008 | Butler et al. |
| 2008/0177260 A1 | 7/2008 | McKinley et al. |
| 2009/0198280 A1 | 8/2009 | Spratt et al. |
| 2010/0145394 A1 | 6/2010 | Harvey et al. |
| 2010/0152787 A1 | 6/2010 | Walsh et al. |
| 2010/0204735 A1 | 8/2010 | Gephart et al. |
| 2010/0298891 A1 | 11/2010 | Jackson |
| 2011/0125195 A1 | 5/2011 | Biedermann et al. |
| 2012/0041495 A9 | 2/2012 | Biedermann et al. |
| 2012/0109218 A1 | 5/2012 | Farris |
| 2012/0185003 A1 | 7/2012 | Biedermann et al. |
| 2012/0232598 A1 | 9/2012 | Hestad et al. |
| 2013/0096623 A1 | 4/2013 | Biedermann et al. |
| 2013/0150904 A1 | 6/2013 | Biedermann et al. |

* cited by examiner

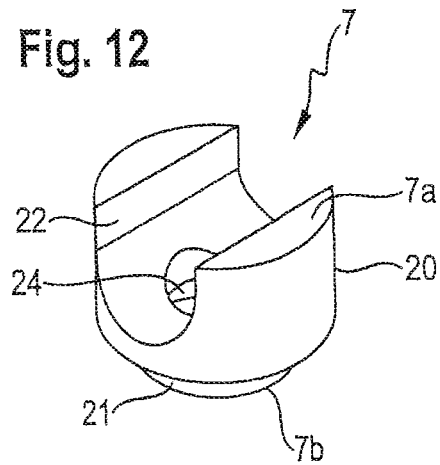
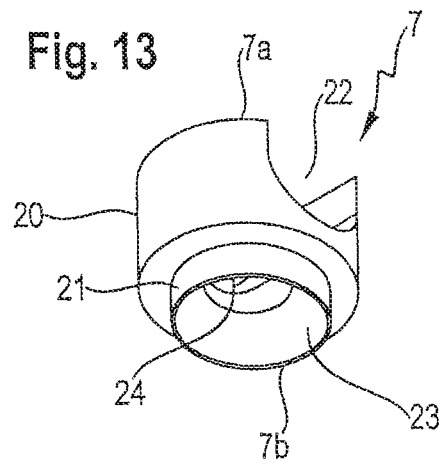
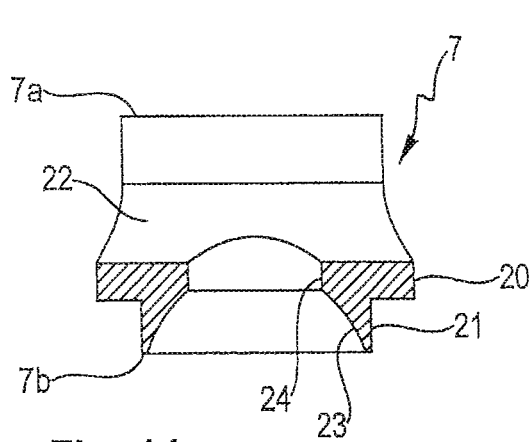
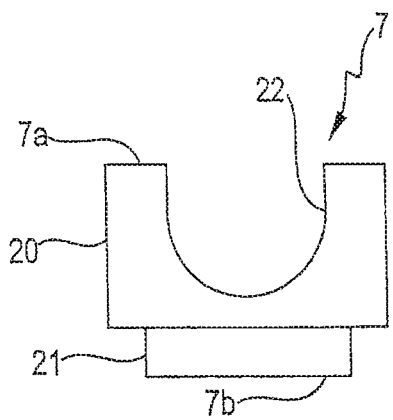
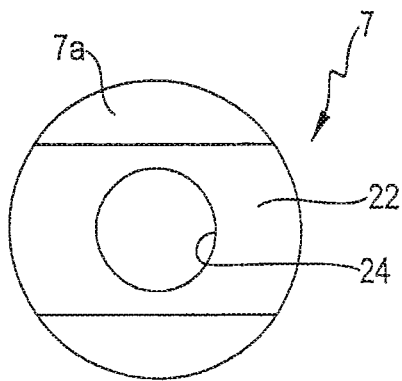

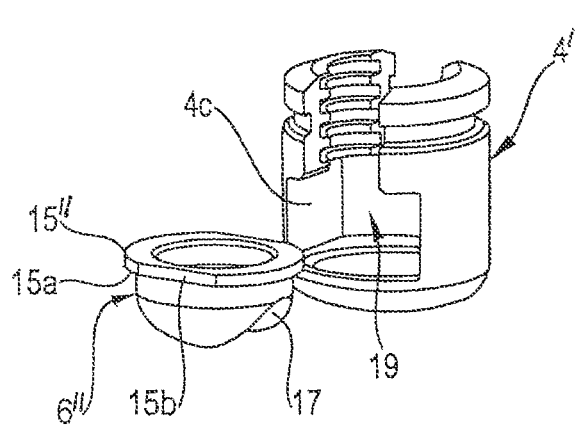
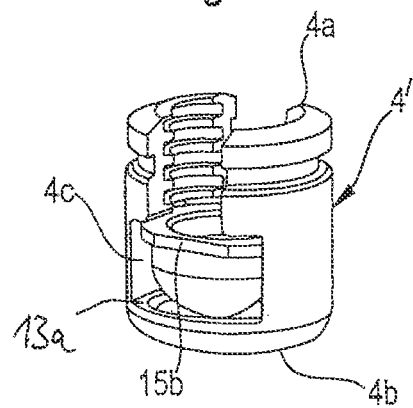
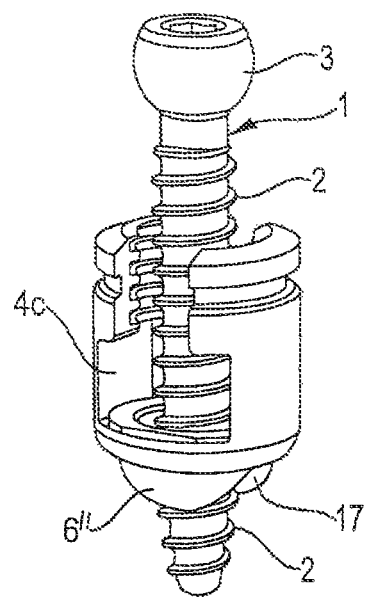
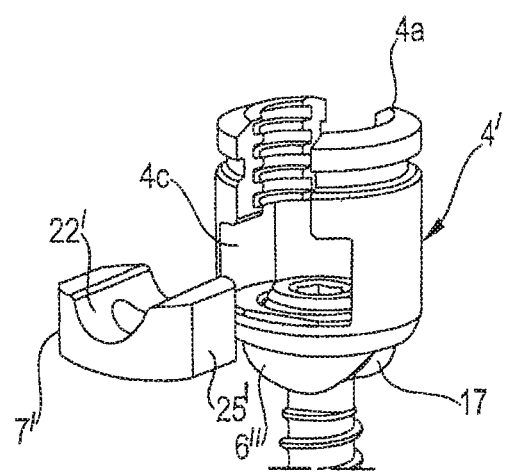

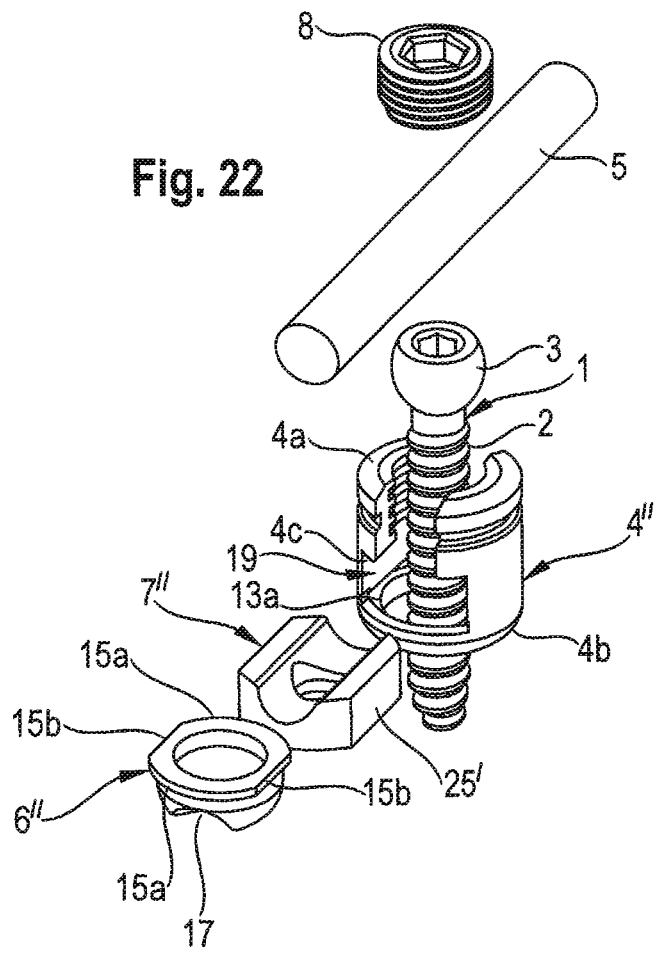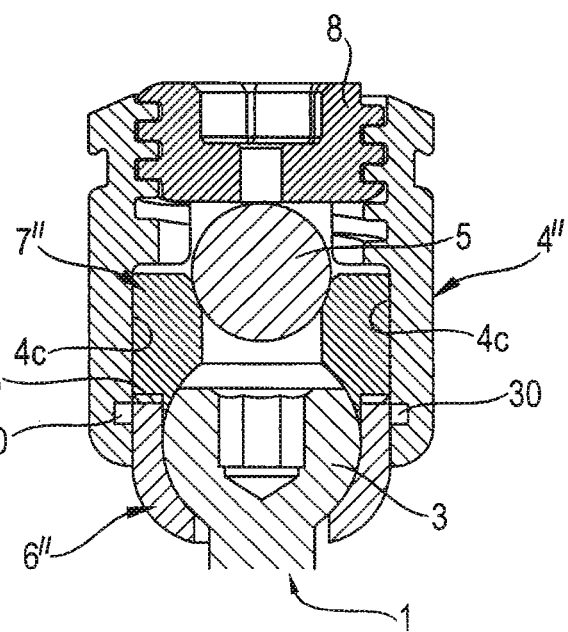

HIGH ANGULATION POLYAXIAL BONE ANCHORING DEVICE

CROSS-REFERENCE TO RELATED APPLICATION(S)

The present application claims the benefit of and priority to U.S. Provisional Patent Application Ser. No. 61/552,019, filed Oct. 27, 2011, the contents of which are hereby incorporated by reference in their entirety.

BACKGROUND

1. Field of the Invention

The invention relates to a polyaxial bone anchoring device that facilitates pivoting of a bone anchoring element at high angles relative to a receiving part. The device includes the bone anchoring element having a shank for anchoring in a bone or a vertebra and a head, and the receiving part for receiving a rod to be connected to the bone anchoring element. An insert piece is rotatably mounted to the receiving part. The insert piece has a seat for the head of the bone anchoring element and is configured to permit the bone anchoring element to pivot at a larger angle at a first location than at a second location relative to the receiving part. The insert piece is supported in the receiving part by a flat surface portion on the receiving part that engages a corresponding flat surface portion of the insert piece.

2. Description of Related Art

A polyaxial bone anchoring device with an enlarged pivot angle is described in U.S. Pat. No. 6,736,820. This bone anchoring device includes a bone screw and a receiving part with a seat for the head of the bone screw. The screw member can be pivoted to at least one side by an enlarged angle, because the edge bounding the free end of the receiving part is of asymmetric construction. In a modified embodiment, an insert piece is provided, which has a spherical bottom as a seat for the head of the screw member.

U.S. 2005/0154391 A1 describes a bone anchor assembly including a bone anchor having a distal shaft configured to engage bone and a proximal member. The proximal member may have a first section and a second section coupled to at least a portion of the bone anchor. The second section may be movably connected to the first section to facilitate relative rotation of the first section and the second section.

U.S. 2007/0118123 A1 describes a polyaxial bone anchor with increased angulation. The polyaxial bone anchor has a locking element shaped and configured to allow an anchoring member, e. g. a screw or a hook, to polyaxially rotate at large angles about a central axis of the bone anchor before compression locking the anchoring member within an anchor head.

SUMMARY

It is an object of embodiments of the invention to provide a polyaxial bone anchoring device with enlarged pivot angle of the bone anchoring element relative to a receiving part that also provides safer fixation.

The polyaxial bone anchoring device according to embodiments of the invention provides for safer fixation because cooperating surfaces providing support for an insert piece are flat. Therefore, higher pressures acting onto a head of the bone anchoring element can be applied. Because the parts are mainly lathe parts, manufacturing is simple and cost-effective. The bone anchoring device according to embodiments of the invention is also easy to assemble.

The bone anchoring device according to embodiments of the invention provides for high angulation, with pivot angles between 30° and to 100° (corresponding to a total range of motion of between 60° and 200°. Due to the high angular ranges, embodiments of the bone anchoring device can also be used for sacral fixation.

Embodiments of the bone anchoring device can be provided as a modular system, with different insert pieces that can be used interchangeably to provide a wide range of higher angulation. Due to such modularity, less inventory is needed, reducing the costs further.

BRIEF DESCRIPTION OF THE DRAWINGS

Further features and advantages will become apparent in the description of embodiments by means of the accompanying drawings. In the drawings:

FIG. 12 shows a perspective view of a pressure element of the polyaxial bone anchoring device according to the first embodiment;

FIG. 13 shows another perspective view of the pressure element of FIG. 12 from below;

FIG. 14 shows a cross-sectional view of the pressure element of the polyaxial bone anchoring device according to the first embodiment, the section being taken in a plane containing the rod axis;

FIG. 15 shows a side view of the pressure element of FIG. 12;

FIG. 16 shows a top view of the pressure element of FIG. 12;

FIGS. 21a to 21d show steps of assembling the polyaxial bone anchoring device according to the third embodiment;

FIG. 22 shows an exploded perspective view of a modified third embodiment of the polyaxial bone anchoring device; and FIG. 23 shows a cross-sectional view of the polyaxial bone anchoring device of FIG. 22 in an assembled state.

DETAILED DESCRIPTION

Figure 1:
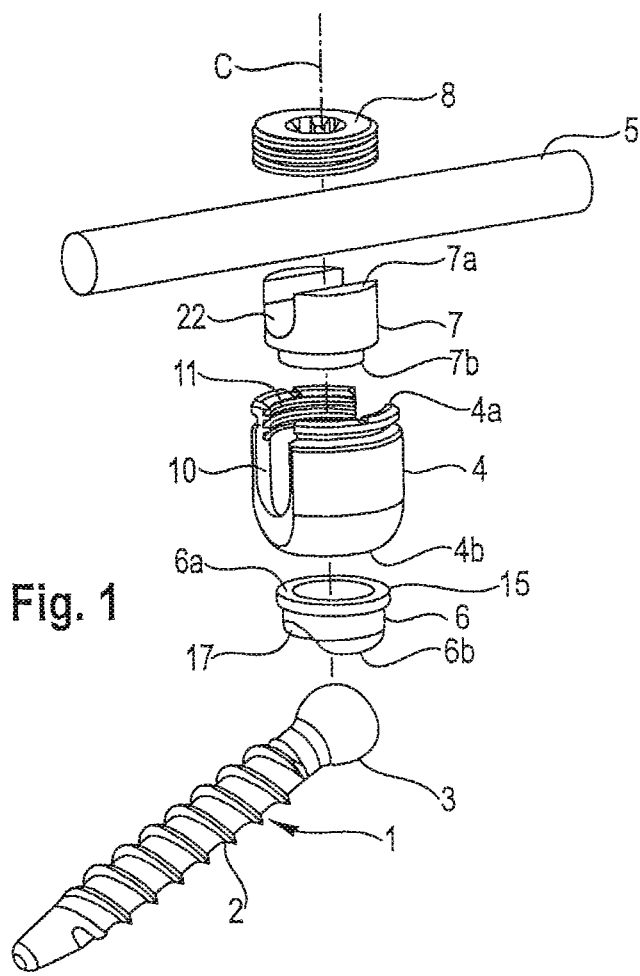
FIG. 1 shows a perspective exploded view of a polyaxial bone anchoring device according to a first embodiment.
Figure 2:
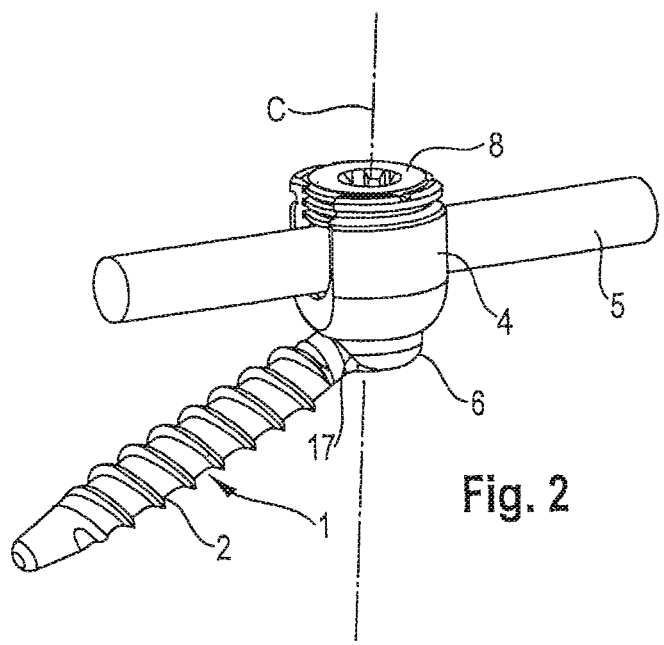
FIG. 2 shows a perspective view of the polyaxial bone anchoring device of FIG. 1 in an assembled state.

Referring to FIGS. 1 to 4, a polyaxial bone anchoring device according to a first embodiment includes a bone anchoring element 1 in the form of, for example, a bone screw having a shank 2 with a threaded section and a head 3. The head 3 has a spherically-shaped outer surface portion and has a recess 3a at its free end for engagement with a driver or tool. The bone anchoring device further includes a receiving part 4 for receiving a rod 5 to be coupled to the bone anchoring element 1. In the receiving part 4, an insert piece 6 providing a seat for the head 3 and a pressure member 7 for exerting pressure onto the head 3 of the bone anchoring element 1 can be arranged. Furthermore, a fixation element in the form of a fixation screw or set screw 8 is provided for securing and fixing the rod 5 in the receiving part 4, and may also contribute to locking the bone anchoring element 1 in place in the receiving part 4.

As can be seen best in FIGS. 5 to 8, the receiving part 4 has a top end 4a and a bottom end 4b, a central axis defining a central axis C of the polyaxial bone anchoring device (see, e.g., FIGS. 3 and 4), and a coaxial first bore 9 extending from the top end 4a in the direction of the bottom end 4b. Adjacent to the top end 4a, a substantially U-shaped recess 10 is provided that forms a channel for receiving the rod 5. By means of the recess 10, two free legs are formed, and are provided with an internal thread 11 configured to cooperate with the fixation screw 8.

At the second end 4b, a coaxial second bore 12 is provided that is in communication with the first bore 9, the second bore 12 having a diameter that is smaller than that of the first bore 9. At the transition between the first bore 9 and the second bore 12, a support surface 13 is formed that extends perpendicular to the central axis C, so that the support surface 13 is substantially flat. In the embodiment shown, the support surface 13 forms an annular shoulder.

Figure 9:
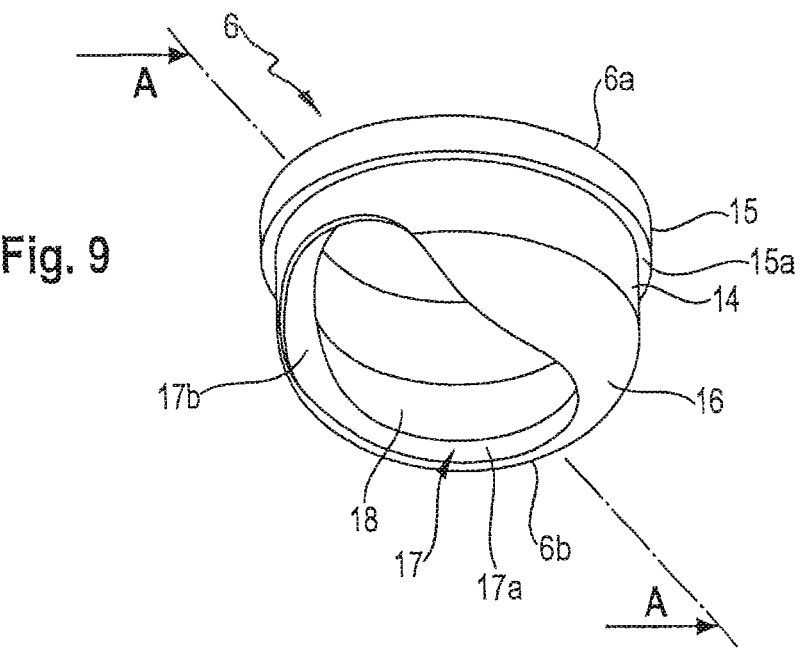
FIG. 9 shows a perspective view of an insert piece of the polyaxial bone anchoring device according to the first embodiment.
Figure 10:
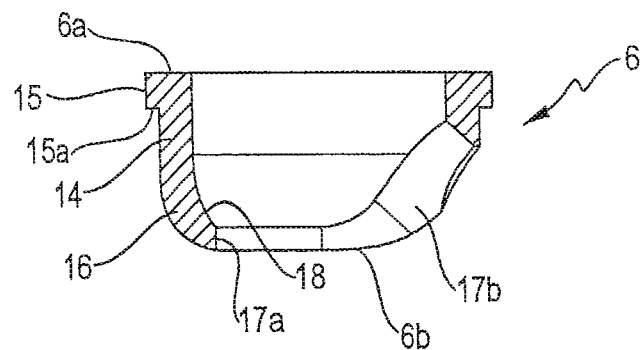
FIG. 10 shows a cross-sectional view of the insert piece of FIG. 9, the section being taken along line A-A in FIG. 9.
Figure 11:
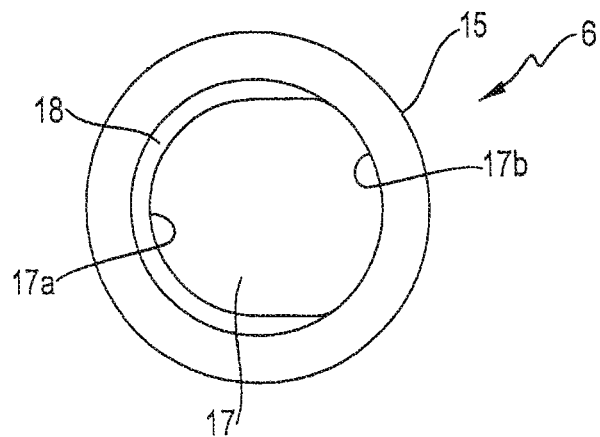
FIG. 11 shows a top view of the insert piece of FIGS. 9 and 10.

As can be seen in FIGS. 9 to 11, the insert piece 6 includes a substantially cylindrical portion, and has a first end 6a and an opposite second end 6b. A hollow cylindrical portion 14 has an inner diameter that is larger than a diameter of the head 3 of the bone anchoring element 1, so that the head 3 can be guided therethrough. An outer diameter of the hollow cylindrical portion 14 is slightly smaller than the inner diameter of the first bore 12 of the receiving part 4. Adjacent the first end 6a, an annular projection 15 is provided that has a flat lower side 15a extending perpendicular to a central axis of the insert piece 6 and that is configured to cooperate with the support surface 13 in the receiving part 4. An outer diameter of the annular projection 15 is slightly smaller than the inner diameter of the first bore 9 and larger than the inner diameter of the second bore 12 of the receiving part 4.

Figure 3:
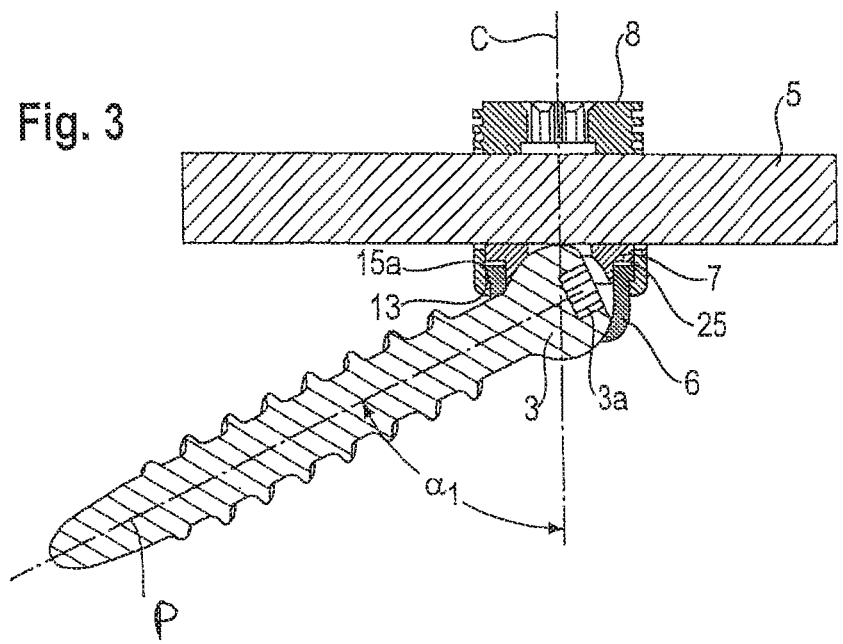
FIG. 3 shows a cross-sectional view of the polyaxial bone anchoring device according to the first embodiment, the section being taken in a plane containing an axis of an inserted rod, and where a the bone anchoring element is pivoted at a first pivot angle to one side.

The insert piece 6 further has a lower portion 16 with an elongate opening 17 at the second end 6b, and with a hollow spherically-shaped section 18 providing a seat for the head 3 of the bone anchoring element 1. An outer surface of the lower portion 16 may have a shape of a spherical segment. However, the lower portion 16 may not necessarily be limited to such shape. The hollow spherically-shaped section 18 is in communication with an inner surface of the hollow cylindrical portion 14. The opening 17 has a partially rounded first portion 17a, as shown in FIGS. 9 and 11, and an elongate second portion 17b extending from the lower portion 16, in some embodiments into the hollow cylindrical portion 14. A width of the opening 17 is larger than an outer diameter of the threaded shank 2 and smaller than the diameter of the head 3 of the bone anchoring element, so that the threaded shank 2 can extend through the opening 17, but the head 3 cannot pass through the opening 17. By means of the opening 17, an axis P of the bone anchoring element 1 forms a maximum pivot angle $\alpha_1$ between a shank axis of the threaded shank 2 and the central axis C when the bone anchoring element 1 is pivoted until the shank 2 abuts against an end of the elongate second portion 17b of the opening 17, as shown in FIG. 3. An edge bounding the opening 17 is an edge that allows the bone anchoring element 1 to pivot at a larger angle relative to the receiving part 4 when the shaft 2 extends into the elongate portion 17b of the opening 17, as seen in FIG. 3, compared to a pivot angle when the shank 2 is at another location, for example, opposite to the elongate portion 17b, as shown in FIG. 4.

Figure 4:
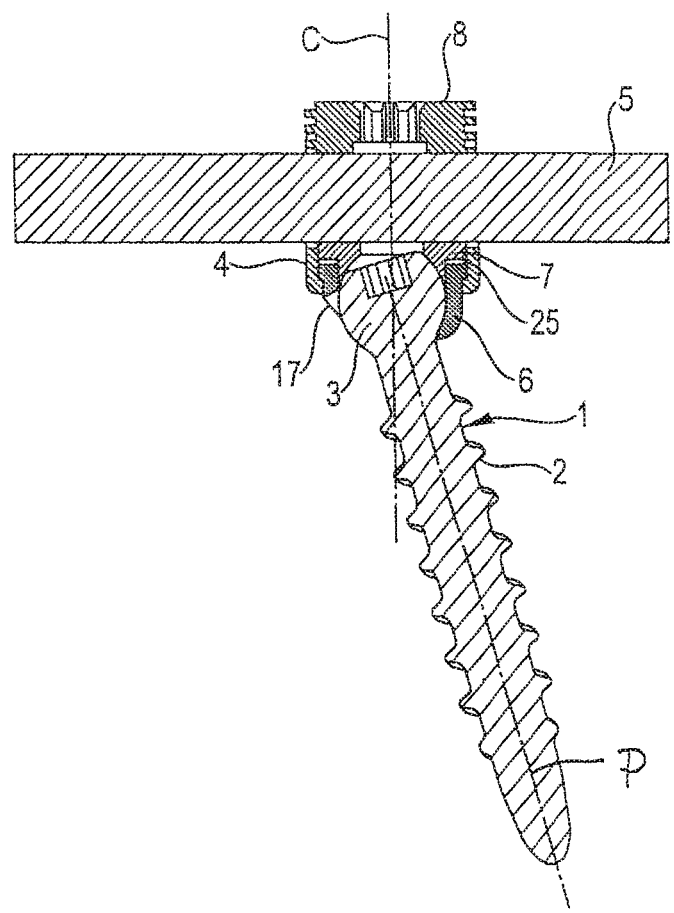
FIG. 4 shows a cross-sectional view of the polyaxial bone anchoring device according to the first embodiment, the section being taken in the plane containing the rod axis, and where the bone anchoring element is pivoted to a second pivot angle at an opposite side compared to FIG. 3.
Figure 5:
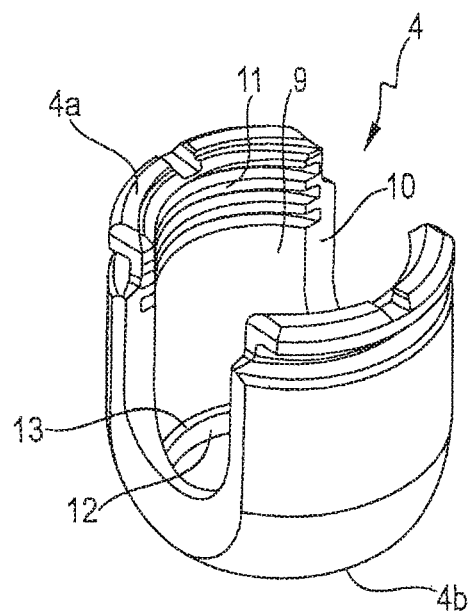
FIG. 5 shows a perspective view of a receiving part of the polyaxial bone anchoring device according to the first embodiment.
Figure 6:
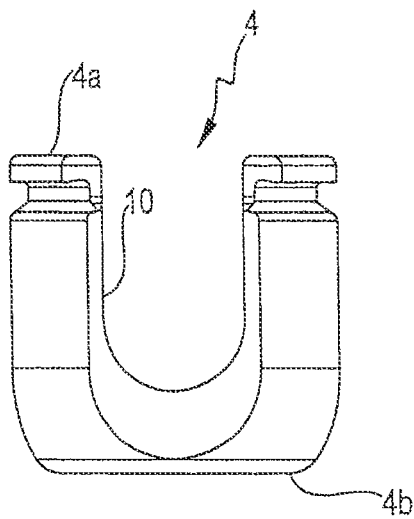
FIG. 6 shows a side view of the receiving part of FIG. 5.
Figure 7:
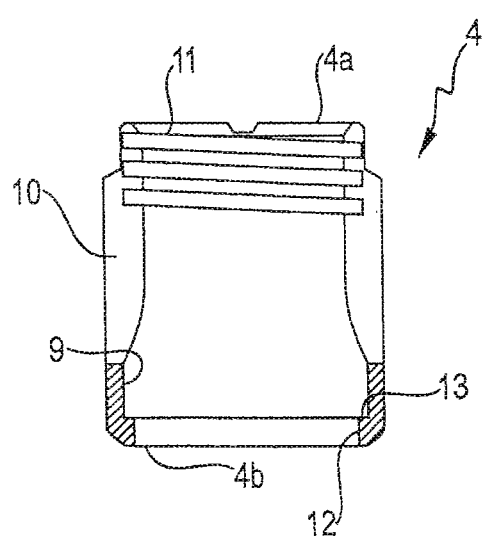
FIG. 7 shows a cross-sectional view of the receiving part of FIG. 5, the section being taken in a plane containing the rod axis.
Figure 8:
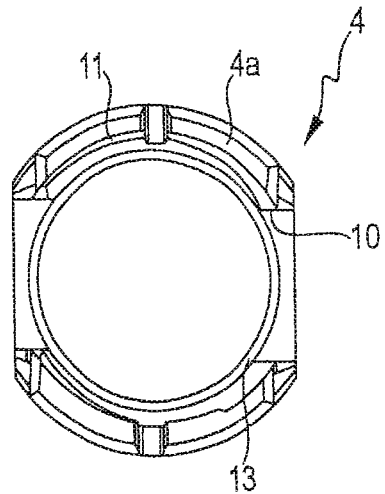
FIG. 8 shows a top view of the receiving part of FIG. 5.

Axial lengths of the hollow cylindrical portion 14 and of the lower portion 16 are such that when the insert piece 6 is inserted into the receiving part 4, as shown in FIGS. 3 and 4, an end of the elongate portion 17b of the opening 17 is flush with or projects slightly out from the second end 4b of the receiving part 4.

The pressure member 7 will now be explained with reference to FIGS. 12 to 16. The pressure member 7 has a first end 7a and an opposite second end 7b, and includes a first cylindrical portion 20 including the first end 7a and a second cylindrical portion 21 including the second end 7b. An outer diameter of the first cylindrical portion 20 is slightly smaller than the inner diameter of the coaxial first bore 9 and an outer diameter of the second cylindrical portion 21 is smaller than the outer diameter of the first cylindrical portion 20. Adjacent the first end 7a, a substantially U-shaped recess 22 is provided that is configured to accommodate the rod 5 therein. Adjacent the second end 7b, a spherical-segment shaped recess 23 is provided with a spherical radius matching a spherical radius of the head 3 of the bone anchoring element 1. Furthermore, a coaxial bore 24 extends between the first end 7a and the second end 7b to allow access to the head 3 with a driver or tool.

As can be seen in FIGS. 3 and 4, the dimensions of the first cylindrical portion 20, the second cylindrical portion 21, and the U-shaped recess 22 are such that when the insert piece 6, the bone anchoring element 1, the pressure member 7, and the rod 5 are inserted into the receiving part 4, the pressure member 7 contacts the head 3 while there is a gap 25 between the first cylindrical portion 20 of the pressure member 7 and the first end 6a of the insert piece 6. Therefore, pressure exerted onto the pressure member 7 is fully transmitted or transferred onto the head 3 and presses the head 3 into the seat 18. The rod 5 projects out of the U-shaped recess 22 of the pressure member 7 so that the fixation element 8 engages the rod 5.

The parts of the bone anchoring device are made of a biocompatible material, such as titanium, stainless steel, of a biocompatible alloy, for example, a nickel titanium Ni—Ti alloy, such as Nitinol, or of a biocompatible plastic material, such as polyetheretherketone (PEEK). The parts can be made of the same material or of different materials.

The bone anchoring device according to the first embodiment can be assembled as follows. First, the insert piece 6 is introduced into the receiving part 4. Then the bone anchoring element 1 is inserted into the receiving part 4, such that the shank 2 extends through the insert piece 6. When the bone anchoring element 1 is fully inserted into the insert piece 6, the head 3 rests in the seat 18 in the insert piece 6. Thereafter, the pressure member 7 can be inserted, and may be preliminarily fixed, for example, through crimping via crimp bores in the receiving part 4 (not shown). Such a preliminary fixation of the pressure member 7 may be such that the pressure member 7 exerts a slight pressure onto the head 3 which holds the receiving part 4 in a preliminary angular position relative to the bone anchoring element 1.

Due to the rotational symmetric design of the upper portion of cylindrical portion 14 and of projection 15 of the insert piece 6, the insert piece 6 can be inserted at any rotational orientation into the receiving part 4.

In use, the bone anchoring element 1 is screwed into a bone or a vertebra, where central axes of the bone anchoring element 1 and of the receiving part 4 may be substantially aligned. Then, the receiving part 4 is pivoted with respect to the bone anchoring element 1. If needed, the receiving part 4 can be pivoted with respect to the bone anchoring element 1 to the maximum pivot angle $\alpha_1$, where the shank 2 abuts against the end of the elongate portion 17b of the opening 17 of the insert piece 6. An orientation of the U-shaped recess 10 of the receiving part 4 can be aligned by rotating the receiving part 4 with respect to the insert piece 6. Because cooperating surfaces of the insert piece 6 and the receiving part 4 are flat surfaces, friction between these surfaces may be enhanced. Therefore, in some embodiments, a preliminary orientation of the insert piece 6 with respect to the receiving part 4 can be maintained by friction. In addition, the corresponding surfaces can have a mechanical structure, such as a roughened structure, to enhance the friction. The insert piece 6 may then be rotated by application of a force greater than the friction force. This allows for more precise adjustments of the orientation of the receiving part 4 relative to the bone anchoring element 1.

A plurality of such bone anchoring devices may be anchored in one or more bones, and their receiving parts 4 may be aligned for insertion of the rod 5. Inserting and tightening of the fixation element 8 of each bone anchoring device locks the respective head 3 relative to the rod 5.

Figure 17:
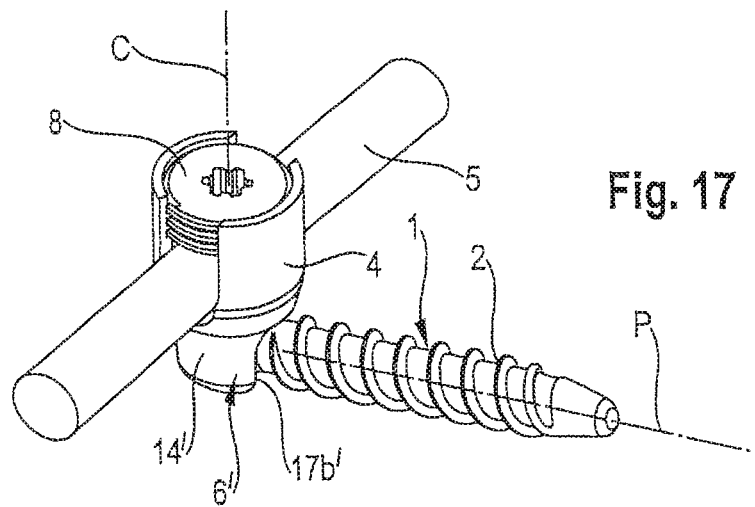
FIG. 17 shows a perspective view of a polyaxial bone anchoring device according to a second embodiment in an assembled state.
Figure 18:
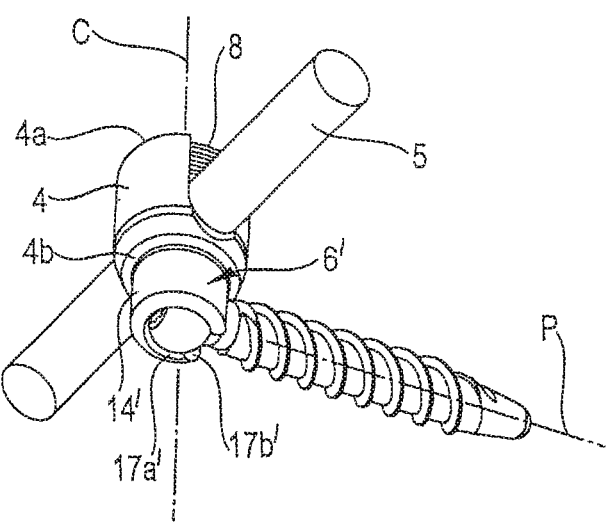
FIG. 18 shows another perspective view of the polyaxial bone anchoring device according to the second embodiment from below.
Figure 19:
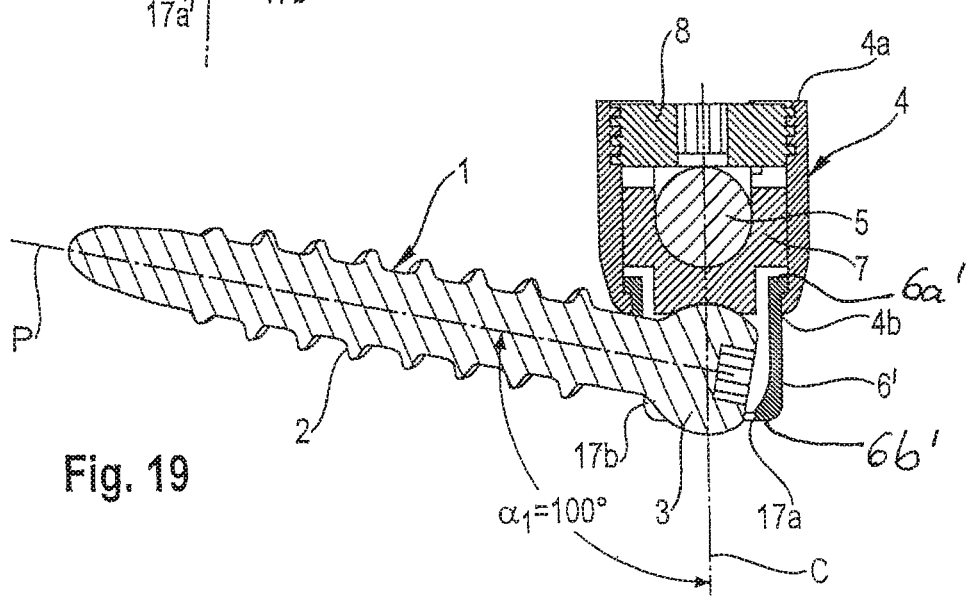
FIG. 19 shows a cross-sectional view of the polyaxial bone anchoring device according to the second embodiment.
Figure 20:
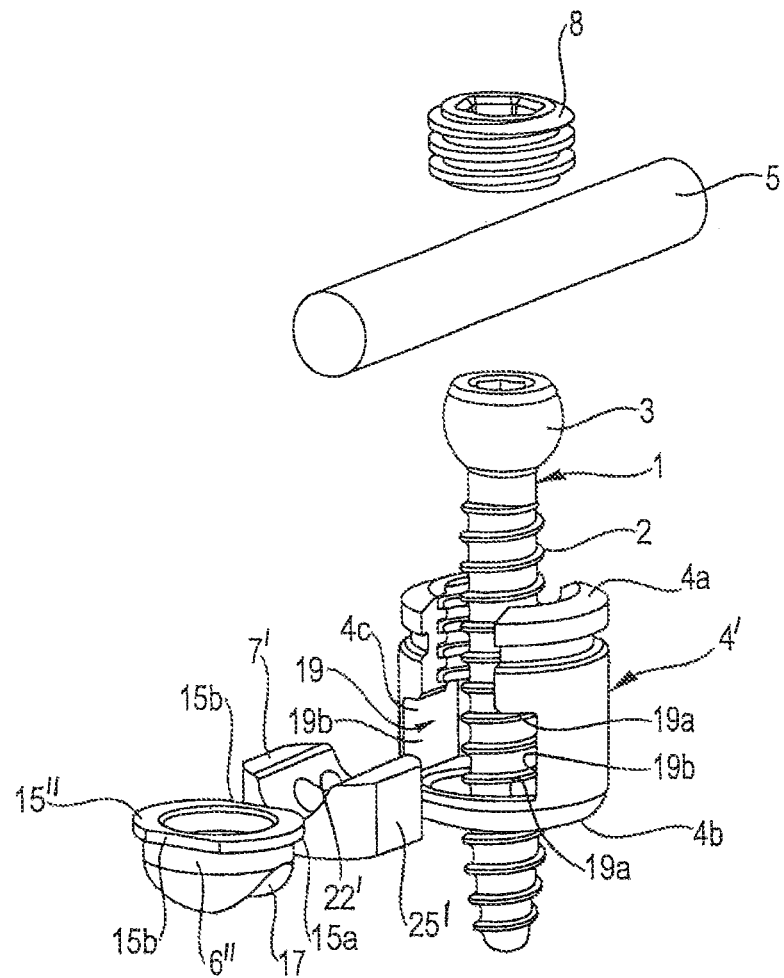
FIG. 20 shows an exploded perspective view of a polyaxial bone anchoring device according to a third embodiment.

Referring to FIGS. 17 to 19, a second embodiment of the bone anchoring device is shown. The second embodiment differs from the first embodiment with respect to the insert piece. All other parts are the same or similar, and are characterized with the same reference numerals and the descriptions thereof are not repeated. The insert piece 6' has a first end 6a' and a second end 6b', and a cylindrical portion 14' that is larger in an axial direction then the cylindrical portion 14 of the first embodiment. Therefore, the insert piece 6' projects farther outward from the receiving part 4 compared to the insert piece 6 according to the first embodiment. The opening 17' has a rounded portion 17a' at the second end 6b' of the insert piece 6' and an elongate substantially U-shaped portion 17b' extending into the wall of the cylindrical portion 14'. Because the cylindrical portion 14' and the opening portion 17b' are longer in an axial direction, it may be possible to pivot the bone anchoring element 1 relative to the receiving part 4 to angles of 90° or more in the second embodiment, for example, to 100° as shown in FIGS. 17 to 19.

With the polyaxial bone anchoring devices described above, a modular system can be provided that includes a receiving part 4 and a bone anchoring element 1, and at least two insert pieces 6, 6' that have cylindrical portions 14, 14' and openings 17b, 17b' with different lengths, to allow pivoting of the bone anchoring element to two different maximum pivot angles.

Referring to FIGS. 20-23, a polyaxial bone anchoring device according to a third embodiment differs from the previous embodiments in that the receiving part 4' has a substantially rectangular opening 19 in its side wall. The opening 19 has long sides 19a extending in a circumferential direction and short sides 19b extending in an axial direction. At its inner wall, the receiving part 4' has two opposite flat portions 4c configured to cooperate with the pressure member 7' described below. The flat portions 4c are located on either side of the opening 19.

The insert piece 6" has a cylindrical projection 15", where on opposite sides two portions are cut away so that two opposite flat sections 15b are formed. The flat sections 15b may facilitate better gripping for insertion, and/or defining an initial alignment position between opening 17' and the rod insertion axis. A diameter of the projection 15" at the rounded sides is slightly smaller than an inner width of the opening 19 corresponding to the long sides 19a.

Similarly, the pressure member 7' has two flat portions 25' on opposite sides of its outer surface, at either end of a cylindrical recess 22'. A width of the pressure member 7' from one flat side 25' to the opposite flat side 25' is smaller than a length of the long side 19a of the opening 19. By means of this, it is possible to insert the insert piece 6" and the pressure member 7' through the opening 19 into the receiving part 4'.

Due to the flattened portions on the pressure member 7' and the insert piece 6" respectively, overall dimensions of the bone anchoring device, in particular with respect to the receiving part 4', can also be reduced.

Assembly of the bone anchoring device according to the third embodiment is shown in FIGS. 21a to 21d. First, the insert piece 6" is inserted through the opening 19 and moved downward until a flat surface 15a at a lower side of projection 15 is supported on a flat surface 13a in the receiving part 4'. Then, as shown in FIG. 21c, the bone anchoring element 1 can be introduced from the first end 4a of the receiving part 4' until its head 3 is seated in the seat 18 of the insert piece 6". Thereafter, the pressure member 7' can be inserted through the opening 19. Such a modular system allows for providing various insert pieces with various angles for the maximum pivot angle, and for selecting a suitable insert piece with the receiving part.

Because the pressure member 7' has two opposite flat portions 25' that cooperate with the flat portions 4c at the inner wall of the receiving part 4', the pressure member 7' is prevented from rotation when in the receiving part 4'.

A polyaxial bone anchoring device according to a modified third embodiment is shown in FIGS. 22 and 23. The receiving part 4" may be even more compact than that shown in FIGS. 20-21d. Between an end of flat portions 4c at an inside of the receiving part 4" near bottom end 4b and support surface 13a for insert piece 6", an undercut portion 30 may be provided on both sides. The undercut portion 30 allows insertion of the insert piece 6" with flat portions 15b aligned with the flat portions 4c of the receiving part 4" through the opening 19, then movement of insert piece 6" downward until it rests on the support surface 13a. The undercut portion 30 is configured to accommodate rounded edges 15a of the insert piece 6", so that the insert piece 6" can be rotated in the receiving part 4" after it has been inserted and moved downward into the receiving part 4".

Further modifications of the embodiments described may also be conceivable. For example, for the bone anchoring element, various different kinds of anchoring elements can be used, for example, screws, canulated screws, or nails. The head and the shank of the bone anchoring elements may also be separate parts that are connectable to each other.

In some embodiments, other kinds of locking devices, including outer nuts, outer caps, bayonet locking devices, and the like, are also possible. The locking device can also be a two-part locking device, having one locking element that locks the head of the bone anchoring element and another locking element that locks the rod.

In addition, while the bounding edge of the insert piece in the described embodiments is asymmetric by means of an elongate opening, an asymmetry that allows a larger pivot angle to one side can also be achieved by other means, for example, by an inclined lower edge of the insert piece.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   a bone anchoring element having a shank for anchoring in a bone or a vertebra and a head;
   a receiving part for receiving a rod to connect the rod to the bone anchoring element, the receiving part having a first end and an opposite second end, a central axis passing through the first and second ends, two legs forming a channel therebetween for receiving the rod, a coaxial first bore at the first end, a coaxial second bore at the second end in communication with the first bore, and a first support surface between the first bore and the second bore that is substantially perpendicular to the central axis;
   an insert piece configured to be assembled and mounted to the receiving part, the insert piece having a seat for pivotably holding the head of the bone anchoring element, a bounding edge with an opening having a width that is smaller than a diameter of the head to prevent passage of the head therethrough, and a second support surface configured to engage the first support surface to support the insert piece relative to the receiving part when the insert piece is mounted to the receiving part, the second support surface formed by a projection at an end of the insert piece opposite the bounding edge; and
   a pressure member configured to be inserted in the receiving part, the pressure member having a surface for contacting the head of the bone anchoring element;
   wherein the insert piece is axially movable from the first end of the receiving part to a position where the first and second support surfaces are engaged while maintaining a rotational orientation in which a portion of the insert piece having the greatest width is radially aligned with at least one of the legs,
   wherein when the insert piece is mounted to the receiving part and the head is in the seat and in contact with the insert piece and the pressure member, the insert piece projects out of the second bore and is rotatable relative to the receiving part and the pressure member, the bounding edge is at an end of the insert piece facing away from the first bore, and the bounding edge is configured to permit the bone anchoring element to pivot at a larger angle at a first location of the bounding edge than at a second location of the bounding edge relative to the central axis.

2. The polyaxial bone anchoring device of claim 1, wherein the first support surface extends circumferentially around the central axis.

3. The polyaxial bone anchoring device of claim 1, wherein the second support surface extends circumferentially around a central axis of the insert piece.

4. The polyaxial bone anchoring device of claim 1, wherein the first support surface comprises an annular projection projecting from an inner wall of the receiving part into the first bore.

5. The polyaxial bone anchoring device of claim 1, wherein the second support surface comprises an annular projection projecting outward from the insert piece.

6. The polyaxial bone anchoring device of claim 5, wherein the annular projection comprises a continuous annular ring.

7. The polyaxial bone anchoring device of claim 1, wherein the insert piece has a first end portion that is rotationally symmetric and a second end portion comprising the bounding edge, wherein the bounding edge is asymmetric.

8. The polyaxial bone anchoring device of claim 1, wherein the insert piece has a recess through which the shank of the bone anchoring element is insertable, wherein the recess is asymmetric with respect to a central axis of the insert piece.

9. The polyaxial bone anchoring device of claim 1, wherein when the insert piece is mounted to the receiving part, a friction force is formed between the first and second support surfaces to hold the insert piece at a first rotational position with respect to the receiving part, and wherein the insert piece is adjustable from the first position by applying a force greater than the friction force to the insert piece or the receiving part.

10. The polyaxial bone anchoring device of claim 1, wherein the pressure member is configured to move in the receiving part along the central axis to exert pressure onto the head.

11. The polyaxial bone anchoring device of claim 1, further comprising a rod and a fixation element for holding a position of the rod relative to the receiving part.

12. A modular polyaxial bone anchoring system comprising:
    a bone anchoring element having a shank for anchoring in a bone or a vertebra and a head;
    a receiving part for receiving a rod to connect the rod to the bone anchoring element, the receiving part having a first end and an opposite second end, a central axis passing through the first and second ends, a channel for receiving a rod, a coaxial first bore at the first end, and a coaxial second bore at the second end in communication with the first bore;
    a first insert piece configured to be assembled and mounted to the receiving part, the first insert piece having a seat and a bounding edge with an opening having a width that is smaller than a diameter of the head to prevent passage of the head therethrough; and
    a second insert piece configured to be assembled and mounted to the receiving part, the second insert piece having a seat and a bounding edge with an opening having a width that is smaller than the diameter of the head to prevent passage of the head therethrough;
    wherein the first insert piece and the second insert piece have different shapes and are interchangeably mountable to the receiving part, and wherein the seat of each of the first and second insert pieces prevents radial movement of a center of the head away from the central axis of the receiving part when the head is in the seat;
    wherein when the first insert piece or the second insert piece is mounted to the receiving part and the head is in the seat of the mounted insert piece, the mounted insert piece projects out of the second bore, the corresponding bounding edge is at an end of the mounted insert piece facing away from the first bore, and the corresponding bounding edge is configured to permit the bone anchoring element to pivot at a larger angle at a first location of the corresponding bounding edge than at a second location of the corresponding bounding edge relative to the central axis; and wherein the larger angle corresponding to the first insert piece is greater than the larger angle corresponding to the second insert piece.

13. The polyaxial bone anchoring system of claim 12, wherein the second insert piece is configured to project farther out from the second bore when mounted to the receiving part than the first insert piece projects out from the second bore when mounted to the receiving part.

14. A method of coupling a rod to a bone anchoring element via a polyaxial bone anchoring device, the bone anchoring element having a shank for anchoring in a bone or a vertebra and a head, the bone anchoring device comprising a receiving part having a first end and an opposite second end, a central axis passing through the first and second ends, two legs forming a channel therebetween for receiving the rod, a coaxial first bore at the first end, a coaxial second bore at the second end in communication with the first bore, and a first support surface between the first bore and the second bore that is substantially perpendicular to the central axis, an insert piece configured to be assembled and mounted to the receiving part, the insert piece having a seat for pivotably holding the head of the bone anchoring element, a bounding edge with an opening having a width that is smaller than a diameter of the head to prevent passage of the head therethrough, and a second support surface configured to engage the first support surface to support the insert piece relative to the receiving part when the insert piece is mounted to the receiving part, the second support surface formed by a projection at an end of the insert piece opposite the bounding edge, a pressure member configured to be inserted in the receiving part, the pressure member having a surface for contacting the head of the bone anchoring element, and a fixation element, the method comprising:

inserting the insert piece into the receiving part and mounting the insert piece to the receiving part, wherein the insert piece is axially movable from the first end of the receiving part to a position where the first and second support surfaces are engaged while maintaining a rotational orientation in which a portion of the insert piece having the greatest width is radially aligned with at least one of the legs;

inserting the shank through the bounding edge of the insert piece until the head is held in the seat of the insert piece;

inserting the pressure member into the receiving part, such that when the insert piece is mounted to the receiving part and the head is in the seat and is in contact with the insert piece and the pressure member, the insert piece projects out of the second bore and is rotatable relative to the receiving part and the pressure member, and the bounding edge is at an end of the insert piece facing away from the first bore;

inserting the shank of the bone anchoring element into a bone or vertebra;

adjusting the receiving part relative to the bone anchoring element, wherein the bounding edge is configured to permit the bone anchoring element to pivot at a larger angle at a first location of the bounding edge than at a second location of the bounding edge;

inserting a rod into the channel of the receiving part; and advancing the fixation element in the channel to lock relative positions of the bone anchoring element, the insert piece, and the rod relative to the receiving part.

15. The method of claim 14, wherein the insert piece is mounted to the receiving part prior to inserting the shank through the bounding edge.

16. The method of claim 14, wherein the insert piece is mounted to the receiving part after inserting the shank through the bounding edge and the head is held in the seat of the insert piece.

17. The method of claim 14, wherein the adjusting the receiving part relative to the bone anchoring element comprises rotating the insert piece relative to the receiving part to adjust a position of the first location of the bounding edge, and adjusting a relative angle of the bone anchoring element relative to the receiving part towards the first location of the bounding edge.

18. The method of claim 14, wherein advancing the fixation element presses the rod against the pressure member, and presses the pressure member against the head of the bone anchoring element to lock the relative positions of the bone anchoring element, the insert piece, and the rod relative to the receiving part.

19. The method of claim 14, wherein the insert piece is a first insert piece, wherein the receiving part further comprises a second insert piece having a seat configured to hold the head and a bounding edge different from the bounding edge of the first insert piece, and wherein the first insert piece and the second insert piece are interchangeably mountable to the receiving part.

20. A modular polyaxial bone anchoring system comprising:

a bone anchoring element having a shank for anchoring in a bone or a vertebra and a head;

a receiving part for receiving a rod to connect the rod to the bone anchoring element, the receiving part having a first end and an opposite second end, a central axis passing through the first and second ends, a channel for receiving a rod, a coaxial first bore at the first end, and a coaxial second bore at the second end in communication with the first bore;

a first insert piece configured to be assembled and mounted to the receiving part, the first insert piece having a seat and a bounding edge with an opening having a width that is smaller than a diameter of the head to prevent passage of the head therethrough; and a second insert piece configured to be assembled and mounted to the receiving part, the second insert piece having a seat and a bounding edge with an opening having a width that is smaller than the diameter of the head to prevent passage of the head therethrough;

wherein the first insert piece and the second insert piece have different shapes and are interchangeably mountable to the receiving part, wherein the seat of each of the first and second insert pieces prevents radial movement of a center of the head away from the central axis of the receiving part when the head is in the seat, and wherein the second insert piece is configured to project farther out from the second bore when mounted to the receiving part than the first insert piece projects out from the second bore when mounted to the receiving part; and wherein when the first insert piece or the second insert piece is mounted to the receiving part and the head is in the seat of the mounted insert piece, the mounted insert piece projects out of the second bore, the corresponding bounding edge is at an end of the mounted insert piece facing away from the first bore, and the corresponding bounding edge is configured to permit the bone anchoring element to pivot at a larger angle at a first location of the corresponding bounding edge than at a second location of the corresponding bounding edge relative to the central axis.

21. The polyaxial bone anchoring system of claim 20, wherein the larger angle corresponding to the first insert piece is greater than the larger angle corresponding to the second insert piece.

* * * * *